US005225063A

United States Patent [19]

Gumbrecht et al.

[11] Patent Number: 5,225,063

[45] Date of Patent: Jul. 6, 1993

[54] APPARATUS FOR THE ELECTROCHEMICAL DETERMINATION OF THE PARTIAL OXYGEN PRESSURE IN A LIQUID MEASURING MEDIUM

[75] Inventors: Walter Gumbrecht, Herzogenaurach; Wolfgang Schelter, Uttenreuth, both of Fed. Rep. of Germany; Roland Hofmann-Tikkanen, Pielavesi, Finland; Walter Preidel, Erlangen, Fed. Rep. of Germany

[73] Assignee: Siemens Aktiengesellschaft, Munich, Fed. Rep. of Germany

[21] Appl. No.: 727,981

[22] Filed: Jul. 10, 1991

[30] Foreign Application Priority Data

Jul. 11, 1990 [EP] European Pat. Off. ........... 90113287

[51] Int. Cl.[5] ............ G01N 27/26

[52] U.S. Cl. ............ 204/402; 204/153.16; 204/153.17; 204/400; 204/403; 204/409; 204/411; 204/412; 204/415

[58] Field of Search ............ 204/400, 412, 415, 403, 204/402, 409, 411

[56] References Cited

U.S. PATENT DOCUMENTS

| | | | |
|---|---|---|---|
| 2,805,191 | 9/1957 | Hersch | 204/153.16 |
| 2,898,282 | 8/1959 | Flook et al. | 204/153.16 |
| 3,227,643 | 1/1966 | Okun et al. | 204/415 |
| 3,912,614 | 10/1975 | Spracklen et al. | 204/415 |
| 4,076,596 | 2/1978 | Connery et al. | 204/153.17 |
| 4,221,567 | 9/1980 | Clark et al. | 23/230 |
| 4,535,786 | 8/1985 | Kater | 128/760 |
| 4,655,880 | 4/1987 | Liu | 204/1 |
| 4,781,798 | 11/1988 | Gough | 204/415 |
| 4,841,974 | 6/1989 | Gumbrecht et al. | 128/635 |
| 4,853,091 | 8/1989 | Mund et al. | 204/1 |

FOREIGN PATENT DOCUMENTS 0353328 2/1990 European Pat. Off. .

OTHER PUBLICATIONS

"Polarographic Determination of Oxygen In Biological Materials Kreuzer", et al., Medical and Biological Applications of Electrochemical Devices, Koryta Ed. 1980, pp. 173-187.

*Primary Examiner*—T. Tung
*Attorney, Agent, or Firm*—Hill, Steadman & Simpson

[57] ABSTRACT

An apparatus for electrochemically determining the partial oxygen pressure $pO_2$ in a liquid measuring medium includes a measuring sensor having a working electrode and a counter-electrode. The electrodes are manufactured in thin-film technology and are arranged on a substrate in a measuring channel, to which the measuring medium and a rinse medium can be supplied in alternation. The measuring channel connects a device which controls the flow rate of the measuring medium to a lumen of a double lumen catheter. The rinse medium is suppliable to a second lumen of the double lumen catheter with reversible flow direction. Both lumens have a common orifice which can be introduced into the measuring medium. So-called poisoning of the electrodes in this arrangement is suppressed because the electrodes are flooded in alternation by the measuring medium in a measuring phase and by the rinse medium in a regeneration phase.

7 Claims, 3 Drawing Sheets

APPARATUS FOR THE ELECTROCHEMICAL DETERMINATION OF THE PARTIAL OXYGEN PRESSURE IN A LIQUID MEASURING MEDIUM

BACKGROUND OF THE INVENTION

1. Field of the Invention

The present invention is directed to an apparatus for electrochemically determining the partial oxygen pressure $pO_2$ of a liquid measuring medium, such as blood, including a measuring sensor provided with a working electrode and a counter-electrode for chemically reducing the oxygen ($O_2$) and having a control means for controlling the potential of the electrodes.

2. Description of the Prior Art

Measuring arrangements for electrochemically determining the partial oxygen pressure $pO_2$ in the blood of a patient are known, and are used for patient monitoring. Knowledge of the partial oxygen pressure, for example, is a necessary condition for assessing the respiratory condition of an artificially respirated patient. The polarographic measuring method (reduction of oxygen) is used as the standard method for measuring the partial oxygen pressure $pO_2$. This oxygen reduction is essentially defined by the electrode material which is used, and by the pre-treatment and composition of a measuring electrolyte. A cathode, which may consist of platinum, is provided as a working electrode, and an Ag/AgCl anode is provided which serves as a counterelectrode. The current through the platinum cathode, upon the application of a defined potential, is a function of the partial oxygen pressure $pO_2$ in the measuring medium. Deposits from the measuring medium on the surface of the platinum cathode may, however, lead to a poisoning of this electrode. A constant recalibration of the electrode system is therefore required.

The problem of electrode poisoning is partially solved in a known arrangement described in "Medical and Biological Applications of Electrochemical Devices", Koryta (1980) at pages 178–179. In this known arrangement, the electrode system contains a platinum cathode as the working electrode and an Ag/AgCl anode, which are provided with an electrolyte and which are covered with a hydrophobic membrane. The membrane allows a gas exchange between the measuring medium and the electrolyte, but prevents the penetration of substances which could cause a poisoning of the electrodes. Because additional substances are required in the electrolyte, given the reduction of oxygen necessary for the measurement, or arise as a result of the measurement, an adequate supply of this electrolyte must be provided. This known arrangement is thus not suitable for miniaturized measuring cells, as are needed for patient monitoring. Moreover, a relatively long time elapses until equilibrium is established between the electrolyte and the measuring medium, thereby preventing rapid measurement of variable partial oxygen pressures $pO_2$.

Another known apparatus is described in U.S. Pat. No. 4,853,091. In this arrangement, an oxygen sensor is provided which has an uncovered electrode, which may consist of precious metal. The working electrode, for example, may consist of gold and the counter-electrode may consist of platinum. In order to prevent poisoning of the working electrode, two different potentials are successively supplied to this electrode, the successive application of the different potentials being referred to as a cycle. Only a portion of the cycle duration is used as a measuring phase, the measuring phase being short compared to the total cycle duration. The cycle thus consists of a relatively short measuring phase and a relatively long regeneration phase. The charge converted at the electrodes serves as measured signal. Evaluation of the measured signal begins with a chronological delay of at least a few milliseconds following the beginning of the measuring phase. In addition to the working electrode and the counter-electrode, this oxygen sensor can be provided with a reference electrode which may consist of silver/silver chloride. The surface of the electrodes is thus in contact with the measuring medium both during the measuring phase and during the regeneration phase.

SUMMARY OF THE INVENTION

It is an object of the present invention to provide an improved apparatus for electrochemical determination of the partial oxygen pressure in a liquid measuring medium, wherein the risk of poisoning of the electrodes is substantially precluded even for a longer operating duration.

In U.S. Pat. No. 4,841,974 (having two inventors in common with the present application), a blood measuring apparatus is disclosed having a measuring channel provided with a measuring sensor and with a reference sensor, the measuring channel being connected to the inner lumen of a double lumen catheter. The outer lumen of the catheter is supplied with infusion solution. Both lumens have a common discharge orifice which can be introduced into the blood. By repeated reversal of the flow direction of the outer lumen by using a reversible pump, the blood and the infusion solution are respectively drawn across the two sensors in alternation in chronological succession. Each of the two sensors thus respectively serves as a measuring sensor and as a reference sensor in alternation.

The method and apparatus disclosed herein constitute an improvement of this known structure. In the apparatus and method disclosed herein, during a relatively short measuring phase, the two electrodes are in at least indirect contact with the measuring medium, and during a relatively long regeneration phase their surfaces are rinsed by a rinsing agent. The rinsing agent is preferably an infusion solution, such as a Ringer solution.

In a further embodiment, a reference electrode may be additionally allocated to the two electrodes of the measuring sensor.

It is also possible to cover the electrodes with a hydrophilic membrane.

Respective electronic amplifiers, preferably operational amplifiers, connected to a control means can be allocated to each of the electrodes. The control means is preferably a computer, such as a personal computer (PC).

DESCRIPTION OF THE PREFERRED EMBODIMENTS

Figure 1:
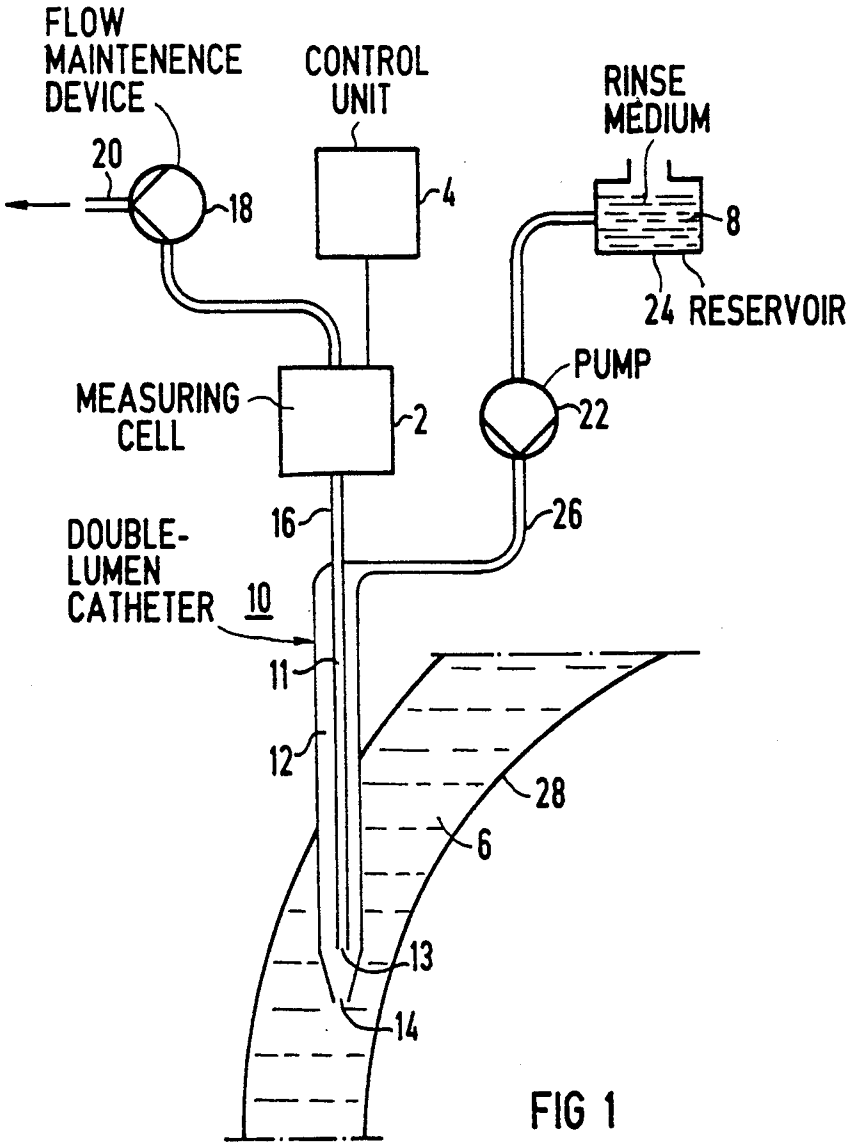
FIG. 1 is a schematic block diagram of an apparatus for the electrochemical determination of the partial oxygen pressure constructed in accordance with the principles of the present invention, and operating in accordance with the principles of the present inventive method.

As shown in FIG. 1, an apparatus for the electrochemical determination of the partial oxygen pressure $pO_2$ in a measuring medium 6, such as blood, includes an electronic control unit 4, which may preferably be a computer, such as a personal computer, which is connected to a measuring cell 2. The measuring cell 2 is a part of a specimen-acquisition system which allows the measuring medium 6 and a rinse medium 8 to alternatingly flow through a measuring channel 16. In this specimen-acquisition system, the measuring channel 16 connects a device 18 for controlling the flow rate in the measuring channel 16 to an inner lumen 11 of a multi-lumen catheter, having at least two lumens and which shall be referred to as a double-lumen catheter 10 for simplification. The inner lumen 11 has an opening 13. The second lumen 12 is connected to a reservoir 24 for a rinse agent 8 via a reversible pump 22. The two lumens 11 and 12 have a common orifice 14. The device 18 may be a pump which ensures a constant flow in the measuring channel 16. A throttle valve, for example, would also be suitable. The measuring cell 2, having an overall length which does not significantly exceed 10 mm, and may amount to considerably less than 10 mm. The measuring cell 2 forms a common structural unit with the double lumen catheter 10, and thus constitutes an extremely compact format for the arrangement, which is generally spatially separated from the device 18 and from the control unit 4.

Figure 2:
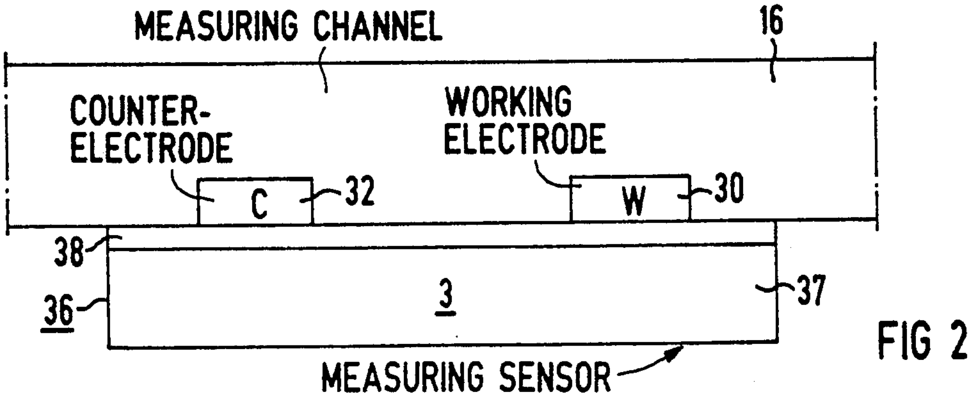
FIG. 2 is an enlarged cross section taken through a measuring cell in the apparatus of FIG. 1, showing a measuring sensor.

As shown in FIG. 2, the measuring cell 2 contains a measuring sensor 3 having a working electrode W referenced 30 and a counter-electrode C referenced 32. The working electrode W and the counter-electrode C are arranged on a substrate 36 which, for example, may consist of a silicon semiconductor member 37 having a surface provided with an insulating layer 38 which may, for example, consist of silicon dioxide $SiO_2$. The working electrode W and the counter electrode C are manufactured in thin-film technology and are arranged so that their respective exposed surfaces in the measuring channel 16 are at least indirectly in contact with the measuring medium 6 or with the rinse medium 8. The working electrode W, which is generally connected as a cathode, preferably consists of a precious metal, such as platinum, or may alternatively consist of carbon. The counter electrode C which simultaneously assumes the function of a reference electrode in the embodiment of FIG. 2, consists of silver/silver chloride and is generally connected as the anode. The thickness of the two electrodes will generally not significantly exceed 200 nm.

As a first step for electrochemically determining the partial oxygen pressure in the measuring medium 6 using the apparatus of FIGS. 1 and 2, the rinse medium 8, preferably an infusion solution, such as a Ringer solution, is first pumped via the pump 22 through an infusion conduit 26 into the outer lumen 12 of the double lumen catheter 10 into the measuring medium 6, such as the blood flow of an artery 28 of a patient. At the same time, a portion of the rinse medium 8 is drawn through the measuring channel 16 of the measuring sensor 2 by the device 18 via the opening 13 of the inner lumen 11, and thus flows over the electrodes W and C of the measuring sensor 3. Upon reversal of the flow at the common orifice 14, for example by reversing the operation of the pump 22, blood is drawn from the artery 28 at the orifice 13 of the inner lumen 11, and flows into the inner lumen 11. As soon as a predetermined amount of the measuring medium 6 has flowed into the measuring channel 16, operation of the pump 22 is again reversed. In the rhythm of the reversal of the pump 22, the device 18 draws an alternating sequence of the measuring medium 6 and the rinse medium 8 through the measuring channel 16 of the measuring cell 2, the total quantity thereof for a measuring event generally not significantly exceeding approximately 20 μl.

Figure 3:
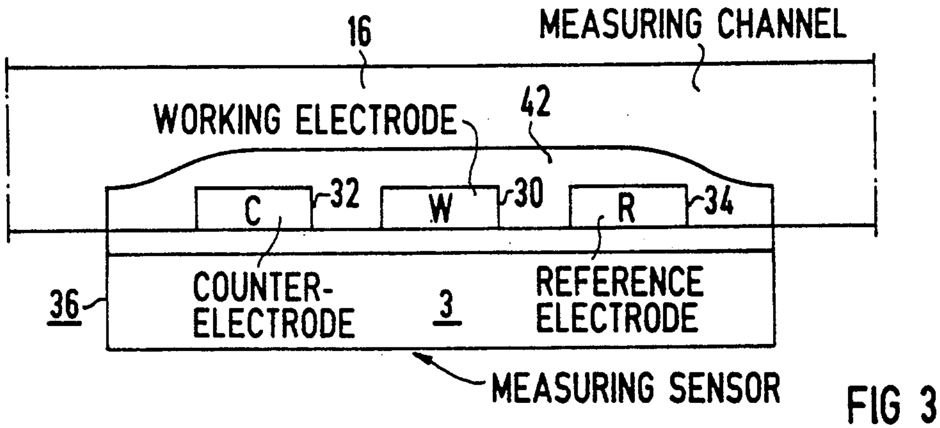
FIG. 3 is an enlarged sectional view taken through a measuring cell, and showing a measuring sensor, in a further embodiment of the invention.

In a further embodiment of a measuring sensor 3 as shown in FIG. 3, the substrate 36 may be provided with a reference electrode R in addition to the working electrode W and the counter electrode C. The reference electrode R is reference 34 in the FIG. 3, and generally consists of silver/silver chloride. In one embodiment, the counter electrode C may consist of precious metal, preferably platinum. The electrodes W, C and R in a preferred embodiment of the measuring sensor 3 may be additionally provided with a hydrophilic membrane 42, which serves as protection against contaminates and deposits. The hydrophilic membrane 42 may, for example, consist of polyhydroxyethylmethacrylate (pHEMA) or of poly(perfluoroalkylene)-sulfonic acid (nafion ®). The measuring medium 6 and the rinse medium 8 flow along this hydrophilic membrane 42 in alternation in the measuring channel 16. During the measuring phase, the oxygen from the measuring medium 6 diffuses through the membrane, and is converted at the working electrode W in accordance with the following reaction:

$$O_2+4e^{(-)}+2H_2O\rightarrow 4OH^{(-)}.$$

Figure 4:
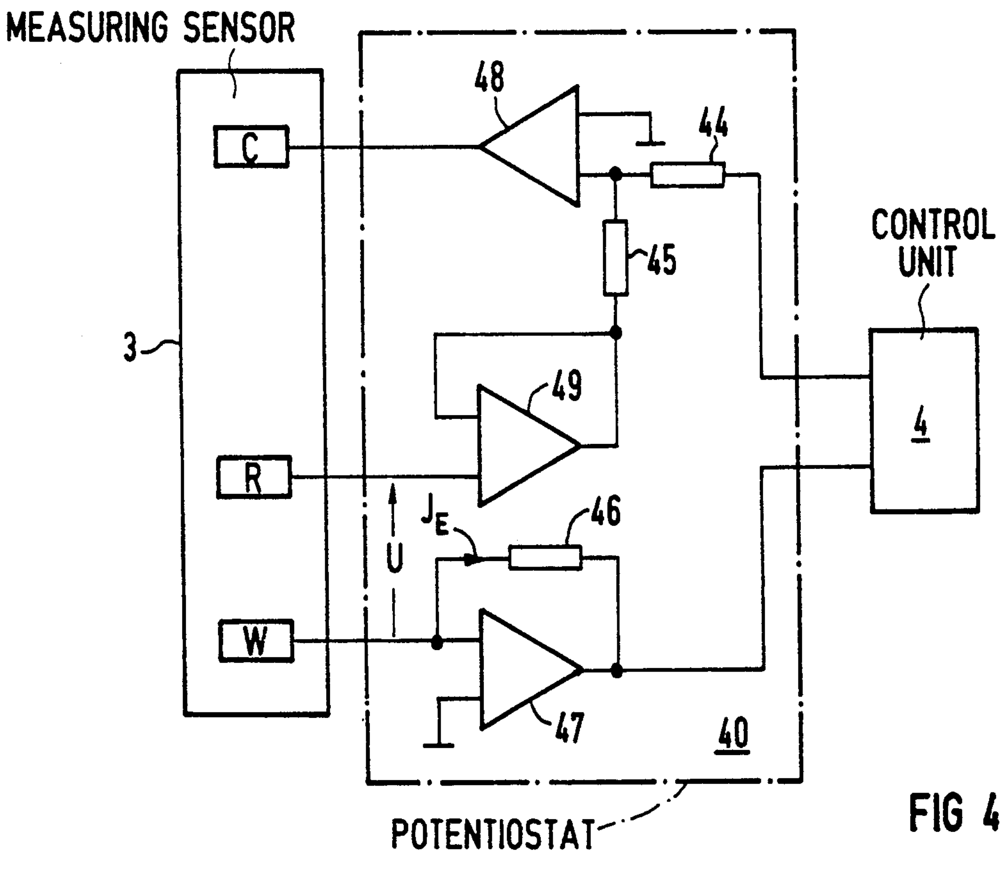
FIG. 4 is a schematic circuit diagram for the electronics associated with the sensor.

This $O_2$ reduction during the measuring phase effects a variation in the electrode current $I_E$ which, preferably after electronic amplification, is supplied to the control unit 4, as schematically shown in FIG. 4. According to FIG. 4, the working electrode W, the counter electrode C and the reference electrode R are connected via a respective amplifiers 47, 48 and 49 to the control unit 4. A voltage divider formed by resistors 44 and 45 is connected at one input of the 44 and 45 amplifier referenced 48. A feedback resistor 46 is connected across the amplifier 47, which acts as a current-to-voltage converter. The amplifier 49 functions as an impedance converter. This overall amplifier circuit forms a potentiostat 40.

The potentiostat 40 may be monolithically integrated in the silicon semiconductor member 37.

Figure 5:
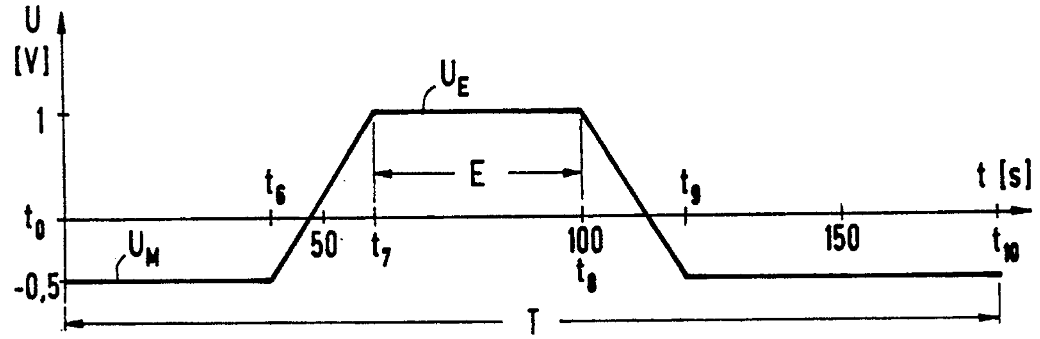
FIG. 5 is a diagram showing the voltage/time relationship of the electrode potential of the working electrode in an apparatus constructed in accordance with the principles of the present invention.
Figure 6:
FIG. 6 is a diagram showing the concentration of the measuring medium over time in an apparatus constructed in accordance with the principles of the present invention.
Figure 7:
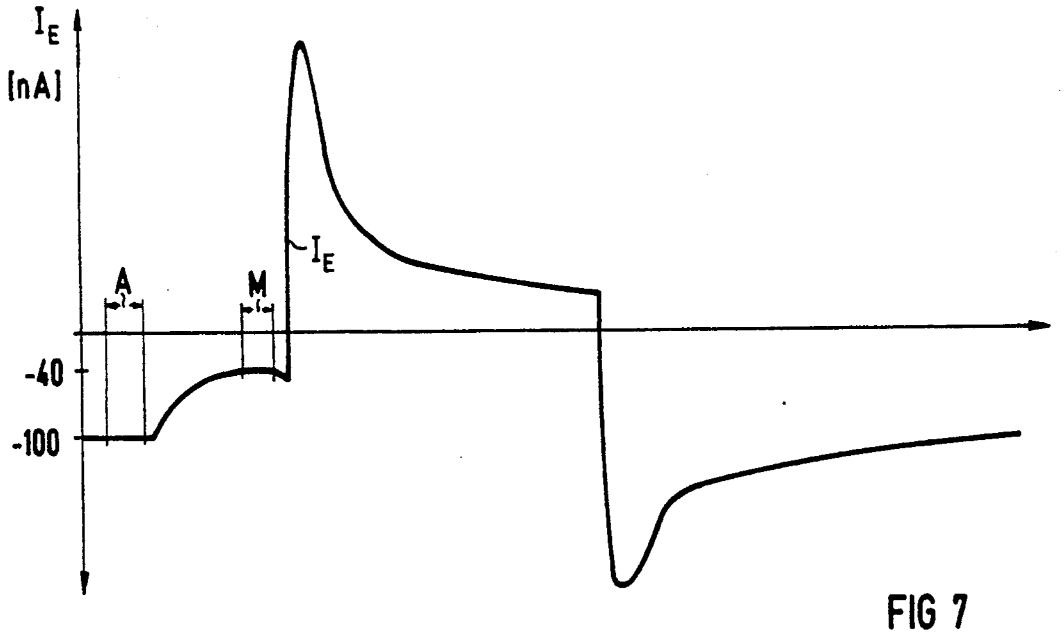
FIG. 7 is a diagram showing the electrode current over time of the working electrode in an apparatus constructed in accordance with the principles of the present invention.

As shown in FIG. 5, wherein the electrode potential U is entered in volts V over time t in seconds, it can be seen that the electrode potential of the working electrode W relative to the reference electrode R (given 0.1 mol $Cl^{(-)}$) amounts, for example, to $U_M=-0.5$ V. In FIG. 6, the concentration $C_M$ of the measuring medium is entered over the working electrode 30 (or over the membrane 42) dependent on the time t when the electrodes are situated in the rinse medium. In FIG. 7, the electrode current $I_E$ is entered in nA over the time t, and it can be seen that the electrode current $I_E$ may amount, for example, to 100 nA. At a time $t_0$, the pump 22 is reversed and draws the measuring medium 6 through the orifice 14 and thus into the inner lumen 11 of the catheter 10. During the time $t_1$ through $t_2$ (a calibration phase A), the rinse medium is still situated at the sensor 3 and the calibration begins by measuring the electrode current. At the end of the calibration phase A at time $t_2$, the concentration $C_M$ of the measuring medium 6 at the sensor 3 increases as shown in FIG. 6. The pump 22 is reversed at time $t_3$. During a relatively short measuring phase M, from $t_4$ through $t_5$, the relative maximum of the electrode current $I_E$ is calculated; according to FIG. 7, this may, for example, amount to $I_E=-40$ nA. Beginning at time $t_6$ which may be, for example, approximately 40 s after $t_0$, transition takes place from the measuring potential of, for example, $U_M=-0.5$ V to a recovery potential of, for example, approximately $U_E=+1$ V at time $t_7$ at approximately 60 s, as shown in FIG. 5. A recovery potential of, for example, $U_E=1$ V is present at the sensor 3 from $t_7$ through $t_8$ during a relatively long regeneration phase E. As shown in FIG. 6, the concentration $C_M$ at the sensor 3 is zero during this regeneration phase E, and the electrodes are situated in the rinse medium. In this time span, substances adsorbed at the working electrode W which may result in electrode poisoning are desorbed and the electrode is thus regenerated. The transition from recovery potential $U_E$ to the measuring potential $U_M$ takes place at time $t_8$ after, for example, approximately 100 s, through $t_9$. A new measuring cycle begins at time $t_{10}$ following a period T of, for example, approximately 180 s.

The above exemplary embodiment has been described in the context of blood as the measuring medium 6, however, the apparatus and method disclosed herein can be used for determining the oxygen content in other media, such as water.

Although modification and changes may be suggested by those skilled in the art, it is the intention of the inventors to embody within the patent warranted hereon all changes and modifications as reasonably and properly come within the scope of their contribution to the art.

We claim as our invention:

1. An apparatus for electrochemically determining the partial oxygen pressure in a liquid measuring medium comprising:

- a measurement cell having a measurement channel;
- a multiple lumen catheter having a first lumen in fluid communication at a first end with a source of rinse solution and a second lumen in fluid communication at a first end with said measurement channel, said first and second lumens having common respective orifices at respective second ends adapted for immersion in said fluid medium;
- a means for maintaining a constant flow of said fluid medium in said second lumen;
- reversible pump means for periodically transferring rinse solution from said source of rinse solution via said first lumen, said common orifices, and said second lumen to said measurement channel so that an alternating sequence of said fluid medium and said rinse solution flows through said measurement channel;
- a thin-film microstructure having a working electrode and a counter electrode disposed in a wall of said measuring channel;
- means for alternatingly simultaneously covering said working electrode and said counter electrode with said fluid medium during a measuring phase and simultaneously covering said working electrode and said counter electrode with said rinse medium during a regeneration phase; and
- measuring circuitry including means for alternatingly electrically connecting said working electrode and said counter electrode to generate a current therebetween in a first direction during said measuring phase for reducing oxygen in said fluid medium and electrically connecting said working electrode and said counter electrode to generate a current therebetween in a second direction during said regeneration phase for desorbing material accumulating on said working electrode, and further including means for measuring said current in said first direction relative to a reference potential during said measuring phase as a measure of said partial oxygen pressure.

2. An apparatus as claimed in claim 1, wherein said microstructure further has a reference electrode also disposed in said wall of said measuring channel, and wherein said means for measuring said current in said first direction is electrically connected to said reference electrode to generate said reference potential at said reference electrode.

3. An apparatus as claimed in claim 2, further comprising a hydrophilic membrane covering said reference electrode, said working electrode, and said counter electrode.

4. An apparatus as claimed in claim 1, further comprising a hydrophilic membrane covering said working electrode and said counter electrode.

5. An apparatus as claimed in claim 1, wherein said working electrode consists of platinum.

6. An apparatus as claimed in claim 1, wherein said working electrode consists of carbon.

7. An apparatus as claimed in claim 1 wherein said means for measuring said current in said first direction is electrically connected to said counter electrode for generating said reference potential at said counter electrode.

* * * * *